United States Patent [19]

Crounse et al.

[11] 3,932,301

[45] Jan. 13, 1976

[54] STILBENE OPTICAL BRIGHTENERS AND COMPOSITIONS BRIGHTENED THEREWITH

[75] Inventors: Nathan N. Crounse; Kantilal B. Desai, both of Cincinnati, Ohio

[73] Assignee: Sterling Drug Inc., New York, N.Y.

[22] Filed: May 29, 1973

[21] Appl. No.: 364,248

Related U.S. Application Data

[63] Continuation-in-part of Ser. No. 118,076, Feb. 23, 1971, Pat. No. 3,781,279.

[52] U.S. Cl. ...... 252/301.2 W; 106/22; 117/33.5 T; 162/162; 252/543; 260/75 T; 260/240 D; 260/243 R; 260/247.7 G; 260/268 TR; 260/293.55; 260/319.1; 260/329 R; 260/330.5; 260/346.2; 260/566 B; 260/570 R; 260/591; 260/600; 260/609 R
[51] Int. Cl.² .......................................... D06L 3/12
[58] Field of Search ...... 252/301.2 W; 260/240 CA, 260/319.1, 240 D

[56] References Cited

UNITED STATES PATENTS 3,697,513   10/1972   Siegrist.................... 252/301.2 W

*Primary Examiner*—Arthur P. Demers
*Attorney, Agent, or Firm*—Lynn T. Fletcher; B. Woodrow Wyatt

[57] ABSTRACT

Benzofurans, benzothiophenes, indoles, naphthofurans and benzofuranobenzofurans which are substituted by 4-vinyl-phenyl groups wherein the 2-position of the vinyl is substituted by a monovalent aromatic radical having one to three aromatic rings are optical brightening agents useful for whitening and brightening natural and synthetic fibers, papers, resins and the like. The compounds are conveniently prepared by interacting benzofurans, benzothiophenes, indoles, naphthofurans or benzofuranobenzofurans which are substituted by a p-tolyl group, with an aromatic aldehyde or preferably the anil derivative thereof.

4 Claims, No Drawings

STILBENE OPTICAL BRIGHTENERS AND COMPOSITIONS BRIGHTENED THEREWITH

This application is a continuation-in-part of our prior copending U.S. Pat. application Ser. No. 118,076, filed Feb. 23, 1971, now U.S. Pat. No. 3,781,279.

This invention relates to compositions of matter classified in the art of chemistry as substituted stilbenes, to processes for their preparation, and to intermediates for the same.

The compounds of this invention are useful as fluorescent whitening and brightening agents for treatment of threads, sheets, films, filaments, textile fabrics, castings, moldings, and the like as well as in the manufacture of textiles, paper, varnishes, inks, coatings and plastics. These compounds are particularly valuable because of their strong blue shade of fluorescence and their excellent stability to light, chlorinetype bleaches and elevated temperatures.

In the first of its compositions of matter aspects, the invention sought to be patented resides in the novel chemical compounds of Formula I

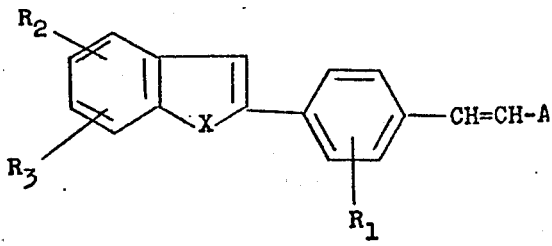

Formula I wherein X is a member of the class consisting of O, S, and N-R, wherein R is H, alkyl having one to six carbon atoms or alkenyl having 2 to 6 carbon atoms; $R_1$ is hydrogen, alkyl having one to six carbon atoms, alkoxy having 1 to 6 carbon atoms or halo; $R_2$ and $R_3$ are the same or different and are members of the class consisting of H, alkyl having 1 to 6 carbon atoms, alkoxy having 1 to 6 carbon atoms, halo, dialkylamino wherein each alkyl has one to six carbon atoms, alkanoylamino having 1 to 6 carbon atoms, phenyl, or phenyl substituted by alkyl having 1 to 6 carbon atoms, halo, alkoxy having 1 to 6 carbon atoms, or alkanoylamino having 1 to 6 carbon atoms; and A is a monovalent aromatic radical having one to three aromatic rings.

In a second composition of matter aspect, the invention sought to be patented resides in the novel chemical compounds of Formula II

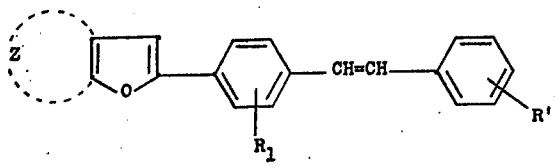

Formula II wherein R' is selected from the class consisting of H, alkyl having 1 to 6 carbon atoms, alkoxy having 1 to 6 carbon atoms, halo, dialkylamino wherein each alkyl group has one to six carbon atoms, alkanoylamino having 1 to 6 carbon atoms, phenyl or phenyl substituted by alkyl having one to six carbon atoms, halo, alkoxy having 1 to 6 carbon atoms, or alkanoylamino having 1 to 6 carbon atoms; $R_1$ has the same significance as in Formula I; and Z is selected from the class consisting of naphtho (that is, 1,2-naphtho, 2,1-naphtho, or 2,3-naphtho) and dibenzofurano (that is, 1,2-dibenzofurano, 2,1-dibenzofurano or 2,3-dibenzofurano).

In a third composition of matter aspect, the invention sought to be patented resides in the novel compounds of Formula III

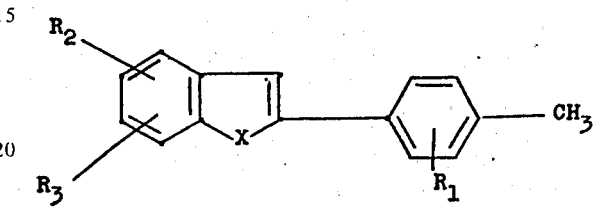

Formula III wherein $R_1$, $R_2$, $R_3$, and X each have the same significance as in Formula I with the provision that when X represents an oxygen atom at least one of $R_1$, $R_2$ and $R_3$ is other than H.

In a fourth composition of matter aspect, the invention sought to be patented resides in the novel compounds of Formula IV

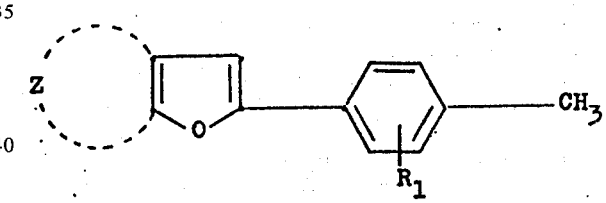

Formula IV wherein $R_1$ has the same significance as in Formulas I, II, and III, and Z has the same significance as in Formula II.

In the first of its process aspects, the invention sought to be patented resides in the method which comprises interacting a compound of Formula III with an aldehyde, A-CHO, or preferably the anil derivative thereof, $A-CH=N-C_6H_5$, wherein A has the same significance as in Formula I to yield a substituted stilbene compound of Formula I.

In a second process aspect, the invention sought to be patented resides in the method which comprises interacting a compound of Formula IV with a benzaldehyde compound,

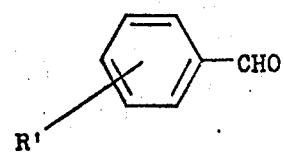

or preferably, the anil derivative thereof of the Formula

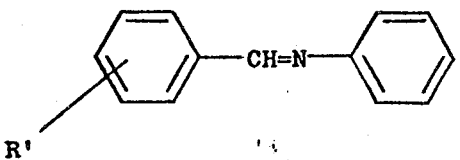

wherein R' has the same significance as in Formula II, to yield a substituted stilbene compound of Formula II.

When $R_1$, $R_2$, $R_3$, and R', in the formulas herein are halo, there are included chloro, fluoro, bromo, and iodo. The preferred halo substituent is chloro because of the relatively low cost and ease of preparation of the required intermediates. However, the other above-named halo substituents are also satisfactory.

When R, $R_1$, $R_2$, $R_3$, and R' in the formulas herein are alkyl having one to six carbon atoms, there are included, for example, methyl, ethyl, propyl, isopropyl, butyl, sec.butyl, tert.-butyl, isobutyl, amyl, hexyl, 2,3-dimethylbutyl, and the like.

When $R_1$, $R_2$, $R_3$, and R' in the formulas herein are alkoxy having one to six carbon atoms, there are included, for example, methoxy, ethoxy, propoxy, isopropoxy, butoxy, isobutoxy, tert.-butoxy, amyloxy, hexyloxy, and the like.

When $R_2$, $R_3$, and R' in the formulas herein are dialkylamino, each alkyl group having from 1 to 6 carbon atoms, there are included for example, dimethylamino, diethylamino, dipropylamino, dibutylamino, dipentylamino, dihexylamino, methylethylamino, N-methyl-N-butylamino, and the like. For the purposes of this invention the common amine radicals wherein the two alkyl groups are joined to form a ring, for example, pyrrolidino, piperidino, morpholino, thiomorpholino, and N-methylpiperazino, are equivalent to the dialkylamino compounds claimed herein.

When $R_2$, $R_3$, and R' are in the formulas herein are alkanoylamino having one to six carbon atoms, there are included, for example, formamido, acetamido, propionamido, butyramido, isobutyramido, valeramido, isovaleramido, caproamido, and the like.

When R in Formulas I and III above is alkenyl having two to six carbon atoms, there are included, for example, alkyl, 2-methyl-2-propenyl, 2-butenyl, 4-pentenyl, 3-methyl-2-butenyl, 2-hexenyl, 3-hexenyl, 1-methyl-2-propenyl, 1,3-dimethyl-2-butenyl, and the like.

When $R_2$, $R_3$, and R' in the formulas herein are substituted phenyl, there are included, for example, p-tolyl, o-tolyl, m-tolyl, p-ethylphenyl, p-acetamidophenyl, o-acetamidophenyl, m-hexanoylaminophenyl, p-chlorophenyl, o-chlorophenyl, m-bromophenyl, o-methoxyphenyl, p-ethoxyphenyl, 2,4-dimethoxyphenyl, 3,4-dichlorophenyl, 2,4-dimethylphenyl, and the like.

In Formula I, A represents a monovalent aromatic radical having one to three aromatic rings. That is, A is a monocyclic, bicyclic, or tricyclic radical having from two to seven conjugated double bonds within the ring system. The rings may be fused as in, for example, the naphthyl radical, or they may be joined in series, as in, for example, the biphenylyl radical. Moreover, the rings may be carbocyclic or heterocyclic. Examples of aromatic rings represented by A in Formula I are phenyl, 2-naphthyl, 1-naphthyl, p-methoxyphenyl, p-chlorophenyl, o-chlorophenyl, 4-biphenylyl, 9-phenanthrenyl, 9-anthryl, 2-benzofuranyl, 2-indolyl, 2-benzothiophenyl, 6-methoxy-2-naphthyl, 2-butoxy-1-naphthyl, 5-bromo-1-naphthyl, 3-coumarinyl, 2-indenyl, 2-quinolinyl, 3-quinolinyl, 2-pyridyl, 3-pyridyl, 4-pyridyl, 2-furanyl, 2-benzoxazolyl, 2-benzothiazolyl, 2-naphtho[2,1-b]furanyl, 2-naphtho[1,2-b]furanyl, and the like.

The compounds of Formulas I and II are useful as fluorescent whitening and brightening agents in treating white and colored fabrics in order to neutralize the yellowness which develops with age in white textiles and to enhance the brilliance of colored textiles. In such utilization the high resistance of these compounds to chlorine bleaches and to light are distinct advantages. Another valuable advantage offered by these compounds is their unusual stability at high temperatures, which permits their use in high melting polymers. They are effectively employed at concentrations in the range of 0.005 to 0.5 percent by weight of the material to be brightened.

The compounds of Formulas III and IV are useful as intermediates for the preparation of the novel fluorescent whitening and brightening agents of Formulas I and II. Moreover, certain of the compounds of Formula IV, for example, 2-(p-tolyl)naphtho[1,2-b]furan, 2-(p-tolyl)naphtho[2,1-b]furan and 2-(p-tolyl)benzothiophene, are also useful as antifertility agents in mammalian animals. In such utilization, tests have shown that, following administration of these compounds to pregnant rats at a dosage level of 100 mg./kg., development of the fetus is terminated, and the fetus is resorbed in the uterus with no noticeable deleterious effects to the mother.

The manner and process of making and using the invention, and the best mode contemplated by the inventor of carrying out the invention, will now be described so as to enable any person skilled in the art to which it pertains to make and use the same.

In general, the compounds of Formulas I and II of this invention are conveniently obtained by interacting an aromatic carboxaldehyde (for example, A-CHO, wherein A has the same significance as in Formula I) or preferably the anil derivative of such aromatic carboxaldehyde, i.e., A—CH=N-$C_6H_5$, with a compound having the structure

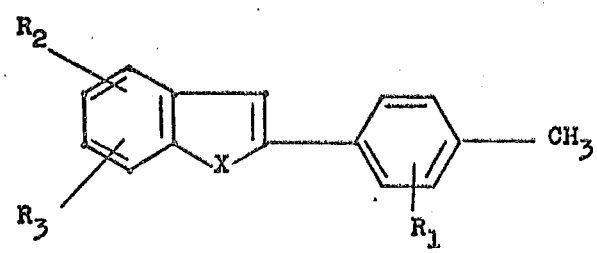

Formula III for making the compounds of Formula I, and the structure

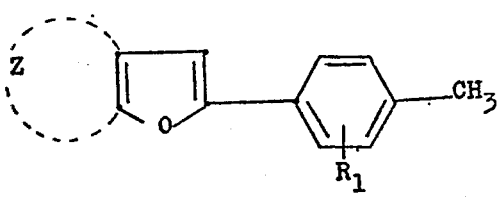

Formula IV for making the compounds of Formula II. The condensation can usually be carried out at rather low temperatures (0–55°C.) in a suitable solvent and in 0°-presence of a strongly alkaline reagent. Under these conditions, the reaction is generally complete in approximately ½ to three hours.

Suitable solvents are those highly polar solvents which are free of acidic hydrogen or other atoms or radicals which may react with strongly alkaline reagents. Examples of suitable solvents include dimethylformamide, dimethylacetamide, diethylformamide, hexamethylphosphoramide, N-formylpiperidine, and sulfolane.

The strongly alkaline reagents suitable for the condensation include the alkali metal salts of tertiary aliphatic alcohols, alkali metal hydroxides, alkali metal amides and alkali metal hydrides. However, the nature of the alkaline reagent (other than its basicity) is not critical to the invention, and any alkaline compound of comparable basicity under the reaction conditions can be employed herein.

Because of the reactive nature of the alkaline reagent, it is preferable to conduct this condensation reaction in a manner which will exclude atmospheric moisture and carbon dioxide. Accordingly, for such purpose an atmosphere of dry nitrogen or other inert gas over the reaction medium is provided.

The intermediate compounds of Formulas III and IV wherein X is O or S are conveniently prepared by cyclizing an appropriately-substituted 4-methylphenacyl ether or thioether of Formula V and Formula VI, respectively:

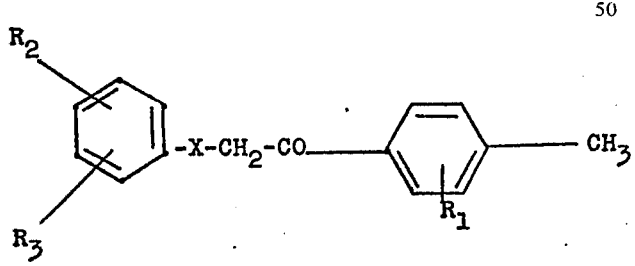

Formula V

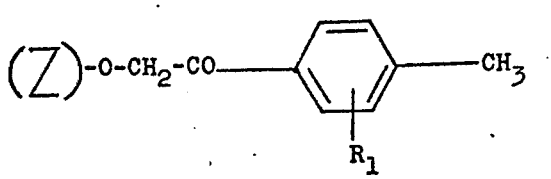

Formula VI wherein $R_1$, $R_2$, $R_3$, and Z have the same meanings as defined above and X is O or S. The cyclization is carried out by heating the phenacyl ether compound in a dehydrating medium, for example, sulfuric acid or preferably polyphosphoric acid, at a temperature in the range 75°–110°C. Cyclization is usually complete in from one to six hours under these conditions. The product of cyclization is then rearranged to the desired intermediates of Formulas III and IV by continued heating at 130°–150°C. in the same reaction medium, as disclosed in the prior art, J. Chem. Soc., 1958, 822.

The requisite 4-methylphenacyl ether intermediates are generally known compounds prepared according to procedure well known to those skilled in the art.

When X in the above formulas represents >N-R, that is, in the case of substituted indoles, the intermediate compounds are conveniently prepared by alkylation of the known compound, 2-(p-tolyl)indole, in accordance with alkylation procedures well known in the art, for example, by interacting 2-(p-tolyl)indole with an alkyl or alkenyl halide in the presence of an alkaline reagent. In this way 2-(p-tolyl)indole can be interacted with, for example, methyl iodide, ethyl bromide, n-propyl bromide, n-butyl bromide, isobutyl bromide, n-hexyl chloride, allyl chloride, 1-bromo-2-pentene, and the like to produce, respectively, 1-methyl-2-(p-tolyl)indole, 1-ethyl-2-(p-tolyl)indole, 1-propyl-2-(p-tolyl)indole, 1-butyl-2-(p-tolyl)indole, 1-isobutyl-2-(p-tolyl)indole, 1(n-hexyl)-2-(p-tolyl)indole, 1-allyl-2-(p-tolyl)indole, 1-(2-pentenyl)-2-(p-tolyl)indole, and the like.

Alternatively, the indole intermediates can be prepared in a manner similar to that employed in preparing the other intermediate 2-(p-tolyl)-substituted compounds disclosed herein, namely, by cyclizing the appropriately-substituted N-(4-methylphenacyl)aniline,

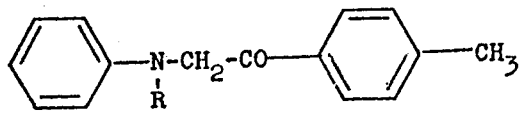

(wherein R is as defined above) by heating said compound with a Lewis acid, for example, zinc chloride, at temperatures of 125°–250°C. in accordance with procedures known to the art.

A preferred mode of utilizing the compounds of Formulas I and II is to incorporate them into melts of synthetic plastic material for spinning synthetic fibers or for casting or molding plastics in an appropriate concentration, for example 0.01 to 0.1 percent by weight of the melt.

A further method of utilizing the compounds of Formulas I and II is to impregnate textile fabrics comprising synthetic fibers, for example polyester (poly[-terephthalic acid ethylene glycol ester]) or nylon, with an aqueous dispersion of the compound at temperatures below about 75°C., for example, at room temperature and then to subject the treated fabric to a dry heat treatment at a temperature above 100°C. The fabric may advantageously be dried at temperatures in the range 60°–100°C. prior to the heat treatment, which is preferably carried out at temperatures in the range 125°–250°C. Said heat treatment may be accomplished by any of several known methods, for example, by heating in a drying chamber, by ironing the fabric, or by treating it with dry superheated steam.

The structures of the compounds of this invention were established by the modes of synthesis, by elementary analysis, and by ultraviolet, infrared, and nuclear magnetic resonance spectra. The course of the reactions and homogeneity of the products were ascertained by thin layer chromatography.

The invention is illustrated by the following examples without, however, being limited thereto. Melting points are uncorrected except where otherwise indicated.

EXAMPLE 1 a. A mixture containing 72.6 g. (0.3 mole) of ω-phenylmercapto-p-methylacetophenone and 325 ml. of polyphosphoric acid was heated to 180°–190°C. for 3 hours. The progress of the reaction was followed by ultraviolet spectroscopy, and the completion of the reaction was shown by the disappearance of the curve characteristics of the starting material and the appearance of a new maximum at 358 nm. The reaction mixture was allowed to cool and was then poured into water. The resulting mixture was collected on a filter and was purified by triturating with dilute sodium hydroxide solution. The resulting product, 2-(p-tolyl)benzothiophene, was collected on a filter, washed free of alkali with water and recrystallized from 2-ethoxyethanol. The resulting pure 2-(p-tolyl)benzothiophene melted at 169°–171°C.

b. A solution containing 6.72 g. (0.03 mole) of 2-(p-tolyl)-benzothiophene and 5.43 g. (0.03 mole) of benzalaniline in 200 ml. of freshly distilled, dry dimethylformamide was flushed with nitrogen for 15 minutes, and 10.08 g. (0.09 mole) of potassium tert.-butoxide was then added with stirring. The color of the reaction mixture progressively changed from red-brown to dark violet to violet and the temperature spontaneously rose from 23° to 32°C. Analysis of an aliquot by ultraviolet spectroscopy showed that the reaction was completed after one hour of stirring. The reaction mixture was added to excess water, the resulting precipitate was collected on a filter, and the filter cake was washed with water. The precipitate was then slurried in hot dimethylformamide and made acidic with 10% aqueous hydrochloric acid. This mixture was then diluted with water, and the precipitate was collected on a filter. The resulting product, 2-(4-stilbenyl)benzothiophene was purified by recrystallization from xylene and by sublimation. The pure 2-(4-stilbenyl)benzothiophene thus obtained melted at 295.5°–296°C. The wavelength of maximum excitation of this compound was 359 nm., and the wavelength of maximum emission was 412 nm.

EXAMPLE 2

Proceeding in a manner similar to that in example 1b above, 2-(p-tolyl)benzothiophene (4.48 g.; 0.02 mole) was interacted with 4.22 g. (0.02 mole) of p-methoxybenzalaniline in the presence of 6.72 g. of potassium tert.-butoxide in 150 ml. of dimethylformamide. Recrystallized from dichlorobenzene, the resulting 2-[4-(p-methoxy)stilbenyl]benzothiophene melted at 307°–308°C. without producing a clear melt. The wavelength of maximum excitation of this compound was 369 nm., and the wavelength of maximum emission was 432 nm.

EXAMPLE 3

Proceeding in a manner similar to that used in Example 1b, 2-(p-tolyl)benzofuran (4.16 g.; 0.02 mole) was interacted with 4.22 g. (0.02 mole) of p-methoxybenzalaniline in the presence of 6.72 g. (0.06 mole) of potassium tert.butoxide in 150 ml. of dimethylformamide. Recrystallized from dichlorobenzene, the 2-[4-(p-methoxy)stilbenyl]benzofuran thus obtained melted at 283°–285°C. The wavelength of maximum excitation of this compound was 369 nm., and the wavelength of maximum emission was 425 nm.

EXAMPLE 4

Proceeding in a manner similar to that used in Example 3 except that benzalaniline was used in place of p-methoxybenzalaniline there was obtained 2-(4-stilbenyl)benzofuran, which, when recrystallized from xylene, melted at 269°–269.5°C. The wavelength of maximum excitation of this compound was 361 nm., and the wavelength of maximum emission was 413 nm.

EXAMPLE 5

When 2-(p-tolyl)benzofuran was condensed with 2-naphthalaniline according to the procedure described in Example 1b there was obtained 2-{4-[2-(naphthyl)vinyl]phenyl}benzofuran which melted at 282°–283°C. following recrystallization from dichlorobenzene. The wavelength of maximum excitation of this compound was 369 nm., and the wavelength of maximum emission was 424 nm.

EXAMPLE 6

Proceeding in a manner similar to that used in Example 3 except that 4-chlorobenzalaniline is used instead of 4-methoxybenzalaniline there was obtained 2-[4-(4'-chlorostilbenyl)]benzofuran which melted at 293°–295°C. when recrystallized from dichlorobenzene. The wavelength of maximum emission was 420 nm., and the wavelength of maximum excitation was 365 nm.

EXAMPLE 7

Proceeding in a manner similar to that used in Example 5 except that 1-naphthalaniline was used in place of 2-naphthalaniline there was obtained 2-{4-[2-(1-naphthyl)-vinyl]phenyl}benzofuran melting at 154°–155°C. when recrystallized from 2-ethoxyethanol. The wavelength of maximum emission of this compound was 439 nm., and the wavelength of maximum excitation was 375 nm.

EXAMPLE 8

Proceeding in a manner similar to that used in Example 3, 3.10 g. (0.015 mole) of 2-(p-tolyl)benzofuran was interacted with 3.85 g. of 4-phenylbenzalaniline in the presence of 5.0 g. (0.054 mole) of potassium tert.-butoxide in 150 ml. of dimethylformamide. Recrystallized from dichlorobenzene and washed with methanol, the 2-(4'-phenyl-4-stilbenyl)benzofuran thus obtained remained unmelted at 350°C. The wavelength of maximum excitation of this compound was 371 nm., and the wavelength of maximum emission was 432 nm.

EXAMPLE 9

Following the procedure outlined in Example 3 except that 9-phenanthrenecarboxaldehyde-N-phenylimine was used in place of p-methoxybenzalaniline, there was obtained 2-{4-[2-(9-phenanthryl)vinyl]phenyl}benzofuran. Recrystallized from toluene, this compound melted at 216°-218°C. The wavelength of maximum excitation of this compound was 373 nm., and the wavelength of maximum emission was 447 nm.

EXAMPLE 10 a. Following the procedure given in Example 1a ω-(β-naphthoxy)-4-methylacetophenone (27.6 g.; 0.1 mole) was heated with 250 ml. of polyphosphoric acid and 25 ml. of methanesulfonic acid at 135°-140°C. for eight hours. The reaction mixture was allowed to cool and was then poured into excess water. The resulting precipitate was collected, washed with 10% sodium hydroxide solution, and then washed free of alkali. Crystallized from ethylene glycol, the resulting 2-(p-tolyl)-naphtho-[2,1-b]furan melted at 141°-142°C.

b. Following the procedure given in Example 1b 2-(p-tolyl)-naphtho-[2,1-b]furan (4.3 g.; 0.016 mole) was interacted with 3.1 g. (0.016 mole) of benzalaniline to produce 2-(4-stilbenyl)-naphtho-[2,1-b]furan, which was purified by recrystallization from xylene. Pure 2-(4-stilbenyl)naphtho[2,1-b]furan thus obtained melted at 248°-250°C. The wavelength of maximum excitation of this compound was 377 nm., and the wavelength of maximum emission was 435.

EXAMPLE 11 a. Following the procedure given in Example 1a ω-(α-naphthoxy)-4-methylacetophenone was heated with polyphosphoric acid to produce 2-(p-tolyl)-naphtho-[1,2-b]furan, which when crystallized from ethylene glycol, melted at 97°-100°C.

b. Following the procedure given in Example 1b the above-named 2-(p-tolyl)-naphtho-[1,2-b]furan was interacted with an equimolar quantity of benzalaniline to produce 2-(4-stilbenyl)naphtho[1,2-b]furan which, when crystallized from xylene and further purified by sublimation, melted at 228°-228.5°C. The wavelength of maximum excitation of this compound was 370 nm., and the wavelength of maximum emission was 426.

EXAMPLE 12

Following the procedure given in Example 1b 2-(p-tolyl)-6-methoxybenzofuran was interacted with an equimolar quantity of benzalaniline to produce 2-(4-stilbenyl)-6-methoxybenzofuran, which, when recrystallized from toluene, melted at 223.5°-225.5°C. The wavelength of maximum excitation of this compound was 371 nm., and the wavelength of maximum emission was 446 nm.

EXAMPLE 13 a. A mixture of 85 g. (0.5 mole) of p-phenylphenol, 84.25 g. (0.5 mole) of p-methylphenacyl chloride, 76.0 g. (0.55 mole) of potassium carbonate 3.75 g. of potassium iodide and 350 ml. of acetone were refluxed with stirring for eight hours. The reaction mixture was allowed to cool and was poured into a large excess of cold water. The precipitate was collected and washed free of alkali with water. Following recrystallization from ethyl alcohol the resulting ω-(4-biphenyloxy)-p-methylacetophenone melted at 101°-102.5°C.

b. Following the procedure given in Example 1a, the above-named ω-(p-biphenyloxy)-4-methylacetophenone was heated with polyphosphoric acid to give 5-phenyl-2-(p-tolyl)benzofuran, which, following recrystallization from 2-ethoxyethanol, melted at 156°-158°C.

c. Following the procedure given in Example 1b, the above-named 5-phenyl-2-(p-tolyl)benzofuran was interacted with an equimolar quantity of β-naphthalaniline to give 5-phenyl-2-{4-[2-(2-naphthyl) vinyl]-phenyl}benzofuran. Recrystallized from dichlorobenzene, this product melted at 287°-288° C. The wavelength of maximum excitation of this compound was 374 nm., and the wavelength of maximum emission was 427 nm.

EXAMPLE 14

When the procedure of Example 13c was repeated using 4-phenylbenzalaniline in place of B-naphthalaniline there was obtained 5-phenyl-2-{4-[2-(4-biphenylyl)vinyl]phenyl}benzofuran which, when recrystallized from dichlorobenzene, melted at 356°-358° C. The wavelength of maximum excitation of this compound was 377 nm., and the wavelength of maximum emission was 434 nm.

EXAMPLE 15 a. Following the procedure given in Example 1a ω-(p-chlorophenoxy)-p-methylacetophenone was heated with polyphosphoric acid to give 5-chloro-2-(p-tolyl)-benzofuran which, when crystallized from 2-ethoxyethanol melted at 183°-186° C.

b. When 5-chloro-2-(p-tolyl)benzofuran was condensed with 4-phenylbenzalaniline as in Example 14 there was obtained 5-chloro-2-{4-[2-(4-biphenylyl)-vinyl]phenyl}benzofuran. When recrystallized from dichlorobenzene this product remained unmelted at 350° C. The wavelength or maximum excitation of this compound was 376 nm., and the wavelength of maximum emission was 431 nm.

EXAMPLE 16 a. Following the procedure given in Example 13a 2,4-dichlorophenol was interacted with an equimolar quantity of 4-methylphenacyl chloride in the presence of potassium carbonate to give w-(2,4-dichlorophenoxy)-p-methylacetophenone. Recrystallized from 2-ethoxyethanol, this product melted at 96.5°-98.5° C.

b. Following the procedure given in Example 1a the above-named ω-(2,4-dichlorophenoxy)-p-methylacetophenone was heated with polyphosphoric acid to give 5,7-dichloro-2-(p-tolyl)benzofuran which, following recrystallization from ethyl ether of ethylene glycol melted at 116°-118° C.

c. Following the procedure given in Example 1b equimolar quantities of the above named 5,7-dichloro-2-(p- tolyl)benzofuran and 4-phenylbenzalaniline were interacted in the presence of potassium tert.-butoxide to give 5,7-dichloro2-{4-[2-(4-biphenylyl)vinyl]phenyl} benzofuran which, following recrystallization from chlorobenzene, melted at 258°–260° C. The wavelength of maximum excitation of this compound was 375 nm., and the wavelength of maximum emission was 431 nm.

EXAMPLE 17

When 5-chloro-2-(p-tolyl)benzofuran (Example 15) was condensed with an equimolar quantity of p-chlorobenzalaniline according to the method of 1b, there was obtained 5-chloro-2-(4'-chloro-4-stilbenyl)-benzofuran, which melted at 280°–282° C., following recrystallization from chlorobenzene. The wavelength of maximum excitation of this compound was 364 nm., and the wavelength of maximum emission was 415 nm.

EXAMPLE 18

The wavelength of maximum excitation of this compound was 364 nm., and the wavelength of maximum emission was 415 nm.

EXAMPLE 18

When the procedure of Example 14 was repeated except that 1-methyl-2-(p-tolyl)indole was used in place of 5-phenyl-2-(p-tolyl)benzofuran, there was obtained 1-methyl2-{4-[2-(4-biphenylyl)vinyl]-phenyl} indole which, when recrystallized from chlorobenzene, melted at 253.5°–254.5° C. The wavelength of maximum excitation of this compound was 365 nm., and the wavelength of maximum emission was 470 nm.

EXAMPLE 19 a. Following the procedure given in Example 13a 2-hydroxydibenzofuran was interacted with 4-methylphenacylchloride in the presence of anhydrous potassium carbonate in acetone to give ω-(2-dibenzofuranyloxy)-p-methylacetophenone. Following recrystallization from 2-ethoxyethanol, this compound melted at 162°–164° C. · b. When the above-named ω-(2-dibenzofuranyloxy)-p-methyl-acetophenone was heated with polyphosphoric acid as in Example 1a there is obtained a mixture of two compounds: 2-p-tolyl)benzofurano[3,2-f]benzofuran and 2-(p-tolyl)benzofurano[3,2-e]benzofuran. The mixture melted at 162°–180° C. following crystallization from 2-ethoxyethanol. The intermediates were not separated at this stage, but rather were carried through to the ultimate products, which were separated in the step which follows.

c. When the procedure of Example 1b was used to interact the above named mixture of 2-(p-tolyl)benzofurano[3,2-f]benzofuran and 2-(p-tolyl)benzofurano[3,2-e]benzofuran with benzalaniline there was obtained a reaction mixture containing 2-(4-stilbenyl)-benzofurano[3,2-f]benzofuran and 2-(4-stilbenyl)benzofurano-[3,2-e]benzofuran. The reaction mixture was filtered and the solid remaining on the funnel was twice recrystallized from dichlorobenzene to obtain purified 2-(4-stilbenyl)benzofurano-[3,2-f]benzofuran which melted at 307°–310°C. The wavelength of maximum excitation of this compound was 382 nm. and the wavelength of maximum emission was 434 nm. Upon evaporation of the reaction mixture filtrate there was obtained 2-(4-stilbenyl)-benzofurano[3,2-e]benzofuran which melted at 239°–241°C. The wavelength of maximum excitation of this compound was 374 nm. and the wavelength of maximum emission was 428 nm.

EXAMPLE 20

When an equivalent amount of the anil derivative of 2-formyl benzofuran is substituted for the benzalaniline in the procedure described in Example 1b above, there is obtained as the product 2-{4-[2-(2-benzofuranyl)-vinyl]phenyl} benzothiophene.

EXAMPLE 21

Following the procedure described in Example 2 above but using an equivalent amount of the anil derivative of 2-formyl indole in place of p-methoxybenzalaniline, there is obtained as the product 2-{4-[2-(2-indolyl)vinyl]phenyl} benzothiophene.

EXAMPLE 22

When an equivalent amount of the anil derivative of 2-formyl benzothiophene is substituted for the p-methoxybenzalaniline in the procedure described in Example 3 above, there is obtained as the product 2-{4-[2-(2-benzothiophenyl)vinyl]-phenyl} benzofuran.

EXAMPLE 23

Following the procedure described in Example 3 above but using an equivalent amount of the anil derivative of 3-formyl coumarin in place of p-methoxybenzalaniline, there is obtained as the product 2-{4-[2-(3-coumarinyl)vinyl]phenyl}-benzofuran.

EXAMPLE 24

When an equivalent amount of the anil derivative of 2-formyl indene is substituted for the 2-naphthalaniline in the procedure described in Example 5 above, there is obtained as the product 2-{4-[2-(2-indenyl)vinyl]-phenyl} benzofuran.

EXAMPLE 25

When an equivalent amount of the anil derivative of 2-formyl quinoline is substituted for the 4-phenylbenzalaniline in the procedure described in Example 18 above, there is obtained as the product 1-methyl-2-{4-[2-(2-quinolinyl)vinyl]-phenyl} indole.

EXAMPLE 26

Following the procedure described in Example 13c above but using an equivalent amount of the anil derivative of 3-formyl quinoline in place of β-naphthalaniline, there is obtained as the product 5-phenyl-2-{4-[2-(3-quinolinyl)vinyl]-phenyl} benzofuran.

EXAMPLE 27

When an equivalent amount of the anil derivative of 2-formyl pyridine is substituted for the 4-phenylbenzalaniline in the procedure described in Example 15c above, there is obtained as the product 5-chloro-2-{4-[2-(2-pyridyl)vinyl]phenyl}-benzofuran.

EXAMPLE 28

Following the procedure described in Example 12 above but using an equivalent amount of the anil derivative of 3-formyl pyridine in place of benzalaniline, there is obtained as the product 6-methoxy-2-{4-[2-(3-pyridyl)vinyl]phenyl}-benzofuran.

EXAMPLE 29

When an equivalent amount of the anil derivative of 4-formyl pyridine is substituted for the 4-phenylbenzalaniline in the procedure described in Example 16c above, there is obtained as the product 5,7-dichloro-2-{4-[2-(4-pyridyl)vinyl]-phenyl}-benzofuran.

EXAMPLE 30

When an equivalent amount of the anil derivative of 2-furfural is substituted for the benzalaniline in the procedure described in Example 1b above, there is obtained as the product 2-{4-[2-(2-furanyl)vinyl]-phenyl}benzothiophene.

EXAMPLE 31

Following the procedure described in Example 18 above but using an equivalent amount of the anil derivative of 2-formyl benzoxazole in place of the 4-phenylbenzalaniline, there is obtained as the product 1-methyl-2-{4-[2-(2-benzoxazolyl)vinyl]-phenyl}indole.

EXAMPLE 32

When an equivalent amount of the anil derivative of 2-formyl benzothiazole is substituted for the 4-phenylbenzalaniline in the procedure described in Example 15b above, there is obtained as the product 5-chloro-2-{4-[2-(2-benzothiazolyl)vinyl]phenyl}-benzofuran.

EXAMPLE 33

Following the procedure described in Example 3 above but using an equivalent amount of the anil derivative of 2-formyl naphtho[2,1-b]furan in place of p-methoxybenzalaniline, there is obtained as the product 2-{4-[2-(2-naphtho[2,1-b]furanyl)vinyl]-phenyl}benzofuran.

EXAMPLE 34

When an equivalent amount of the anil derivative of 9-formyl anthracene is substituted for the 4-phenylbenzalaniline in the procedure described in Example 16c above, there is obtained as the product 5,7-dichloro-2-{4-[2-(9-anthryl)vinyl]-phenyl}benzofuran.

EXAMPLE 35

When an equivalent amount of the anil derivative of 2-formyl naphtho[1,2-b]furan is substituted for the benzalaniline in the procedure described in Example 1b above, there is obtained as the product 2-{4-[2-(2-naphtho[1,2-b]furanyl)vinyl]phenyl}benzothiophene.

EXAMPLE 36

When an equivalent amount of the benzalaniline is substituted for the 4-phenylbenzalanile in the procedure described in Example 18 above, there is obtained as the product 1-methyl-2-(4-stilbenyl)indole which, when recrystallized from 2-ethoxyethanol, melted at 163°–164° C. The wavelength of maximum excitation of this compound was 352 nm, and the wavelength of maximum emission was 455 nm.

When the appropriate p-tolyl-substituted compound of Formula III or of Formula IV and the anil derivative of the appropriate aldehyde are interacted in a manner similar to that described in Example 1b, there are obtained:

5-(1-Methylpropyl)-2-(2'-chloro-3-fluoro-4-stilbenyl)benzofuran from the interaction of 5-(1-methylpropyl)-2-(3-fluoro-4-tolyl)-benzofuran and o-chlorobenzalaniline;

7-n-Hexyl-2-(4'-methoxy-3-iodo-4-stilbenyl)benzofuran from the interaction of 7-n-hexyl-2-(3-iodo-4-tolyl)benzofuran and p-methoxybenzalaniline;

5-n-Propyl-7-ethyl-2-(4'-acetamido-3-methoxy-4-stilbenyl)benzofuran from the interaction of 5-n-propyl-7-ethyl-2-(3-methoxy4-tolyl)benzofuran and p-acetamidobenzalaniline;

5,7-Di-n-hexyl-2-(4'-chloro-3-n-pentyl-4-stilbenyl)-benzothiophene from the interaction of 5,7-di-n-hexyl-2-(3-n-pentyl-4-tolyl)benzothiophene and p-chlorobenzalaniline;

4-Methoxy-7-bromo-2-(2'ethoxy-3-bromo-4-stilbenyl)benzothiophene from the interaction of 4-methoxy-7-bromo-2-(3-bromo-4-tolyl)benzothiophene and o-ethoxybenzalaniline;

5-dimethylamino-2-(3,4'-diisopropyl-4-stilbenyl)-benzothiophene from the interaction of 5-dimethylamino-2-(3-isopropyl-4-tolyl)-benzothiophene and p-isopropylbenzalaniline;

6-(4-Chlorophenyl)-2-(4'-dimethylamino-3-bromo-4-stilbenyl)benzofuran from the interaction of 6-(4-chlorophenyl)-2-(3-bromo-4-tolyl)benzofuran and p-dimethylaminobenzalaniline;

5-(4-Ethylphenyl)-2-(4'-diethylamino-3-chloro-4-stilbenyl)benzothiophene from the interaction of 5-(4-ethylphenyl)-2-(3-chloro-4-tolyl)benzothiophene and p-diethylaminobenzalaniline;

1-Ethyl-5-n-hexyl-2-(3-bromo-4-stilbenyl)indole from the interaction of 1-ethyl-5-n-hexyl-2-(3-bromo-4-tolyl)indole and benzalaniline;

1-n-Hexyl-2-{2-n-propyl-4-[2-(9-phenanthryl)-vinyl]phenyl}indole from the interaction of 1-n-hexyl-2-(3-n-propyl-4-tolyl)indole and 9-phenanthrenecarboxaldehyde-N-phenylimine;

5,7-Diethoxy-2-{2-chloro-4-[2-(2-naphthyl)vinyl]-phenyl}indole from the interaction of 5,7-diethoxy-2-(3-chloro-4-tolyl)indole and β-naphthalaniline;

1-Allyl-6-bromo-5-fluoro-2-{2-n-butyl-4-[2-(4-biphenylyl)vinyl]-phenyl}indole from the interaction of 1-allyl-6-bromo-5-fluoro-2-(3-n-butyl-4-tolyl)indole and 4-phenylbenzalaniline;

1-t-Butyl-5-(4-methoxyphenyl)-2-{2-isopropyl-4-[2-(2-indolyl)-vinyl]phenyl}indole from the interaction of 1-t-butyl-5-(4-methoxyphenyl)-2-(3-isopropyl-4-tolyl)indole and the anil derivative of 2-formyl indole;

5-Fluoro-7-iodo-2-{2-iodo-4-[2-(2-pyridyl)vinyl]-phenyl}benzofuran from the interaction of 5-fluoro-7-iodo-2-(3iodo-4-tolyl)benzofuran and the anil derivative of 2-formyl pyridine;

5-n-Hexyloxy-2-{2-n-pentyl-4-[2-(2-naphtho[2,1-b]furanyl)vinyl]phenyl}benzothiophene from the interaction of 5-n-hexloxy-2(3-n-pentyl-4-tolyl)benzothiophene and the anil derivative of 2-formyl naphtho[2,1-b]furan;

5-Acetamido-2-{2-n-butyl-4-[2-(6-methoxy-2-naphthyl)vinyl]phenyl}-benzothiophene from the interaction of 5-acetamido-2-(3-n-butyl-4tolyl)benzothiophene and 6-methoxy-2-naphthalaniline;

6-Methoxy-7-isopropoxy-2-{2-n-propyl-4-[2-(5-bromo-1-naphthyl)-vinyl]phenyl}benzofuran from the interaction of 6-methoxy-7-isopropoxy-2-(3-n-propyl-4-tolyl)benzofuran and 5-bromo-1-naphthal-aniline;

2-{2-Bromo-4-[2-(4-isopropylpheny)vinyl]phenyl- } naphtho[2,1-b]-furan from the interaction of 2-(3-bromo-4-tolyl)-naphtho[2,1-b]furan and p-isopropylbenzalaniline;

2-{2-n-Propyl-4-[2-(4-methoxyphenyl)vinyl]phenyl} naphtho[1,2-b]-furan from the interaction of 2-(3-n-propyl-4-tolyl)-naphtho[1,2-b]furan and p-methoxybenzalaniline;

2-{2-Iodo-4-[2-(2-ethoxyphenyl)vinyl]phenyl} naphtho[2,3-b]furan from the interaction of 2-(3-iodo-4-tolyl)-naphtho[2,3-b]furan and o-ethoxybenzalaniline;

2-{2-n-Butyl-4-[2-(4-chlorophenyl)vinyl]phenyl- } benzofurano[3,2-f]-benzofuran from the interaction of 2-(3-n-butyl-4-tolyl)benzofurano[3,2-f]benzofuran and p-chlorobenzalaniline;

2-{2-Methoxy-4-[2-(4diethylaminophenyl)vinyl]-phenyl} benzofurano[3,2-e]benzofuran from the interaction of 2-(3-methoxy-4-tolyl)-benzofurano[3,2-e]benzofuran and p-diethylaminobenzalaniline;

2-{2-n-Pentyl-4-[2-(4-acetamidophenyl)vinyl]-phenyl} benzofurano [2,3-f]benzofuran from the interaction of 2-(3-n-pentyl-4-tolyl)-benzofurano[2,3-f]benzofuran and p-acetamidobenzalaniline;

2-{2-Bromo-4-[2-(3'-chloro-4'-methoxy-4-biphenylyl)vinyl]phenyl} -naphtho[2,1-b]furan from the interaction of 2-(3-bromo-4-tolyl)-naphtho[2,1-b]furan and 4-(3-chloro-4-methoxyphenyl)benzalaniline; 2-{2-n-Butyl-4-[2-(4-biphenylyl)vinyl]phenyl} benzofuran from the interaction of 2-(3-n-butyl-4-tolyl)naphtho[2,3-b]furan;

2-[4-(4'-n-Pentyl)stilbenyl]benzofurano[3,2-f]benzofuran from the interaction of 2-(p-tolyl)benzofurano[3,2-f]benzofuran and 4-n-pentylbenzalaniline;

2-[4-(4'-n-Hexyloxy)stilbenyl]benzofurano[2,3-f]benzofuran from the interaction of 2-(p-tolyl)benzofurano[2,3-f]benzofuran and 4-n-hexyloxybenzalaniline;

2-{2-n-Propyl-4-[2-(4-bromophenyl)vinyl]phenyl- } naphtho[1,2-b]-furan from the interaction of 2-(3-n-propyl-4-tolyl)naphtho[1,2-b]furan and p-bromobenzalaniline; and 2-{2-Methoxy-4-[2-(4-fluorophenyl)vinyl]phenyl- } benzofurano [3,2-e]benzofuran from the interaction of 2-(3-methoxy-4-tolyl) benzofurano[3,2-e]benzofuran and p-fluorbenzalaniline.

The effectiveness of the optical brightening agents, prepared as above, when incorporated into polyethylene terephthalate melts was tested as follows:

A solution of 5-chloro-2-{4-[2-(4-biphenylyl)vinyl]-phenyl} benzofuran (Example 15b) in dimethyl terephthalate was prepared by intermixing 0.04 gr. of the brightener with 10.00 gr. of dimethyl terephthalate and then melting the two solids together, with continual stirring and under a carbon dioxide atmosphere, by immersing the container in a bath of diethyl phthalate which was then heated to 200° C. during a period of about 15–20 minutes. The fluid mixture was then poured into a mortar and ground to a fine powder. The solid solution of brightener in dimethyl phthalate was incorporated into polyethylene terephthalate by blending 1.5 g. of the brightener-dimethyl terephthalate powder with 18.0 g. of predried polyethylene terephthalate chips and 0.5 g. of dimethyl terephthalate. The mixture was melted under a carbon dioxide atmosphere by immersing the container in a bath of diethyl phthalate at 115° C. after which the bath was heated to boiling (295°–7° C. The melt was stirred for five minutes, and it then was removed from the bath and allowed to cool to room temperature, continually under carbon dioxide. The polyethylene terephthalate casting was then broken up and ball milled with stoneware pellets in distilled water. The particles were dried and screened, and those passing through a 40 mesh screen were packed into a 5 cm. polystyrene Petri dish. The color of the sample was then measured on a color difference meter (Hunterlab Model D-25, Hunter Associates Laboratory, McLean, Va.) in comparison with a standard magnesium oxide plate. These values were then compared with a blank sample prepared in the identical way except that the optical brightener was omitted. Following are the readings obtained in comparison with the standard magnesium oxide plate:

| Hunterlab D-25 Readings | L | a | b |
|---|---|---|---|
| Blank polyethylene terephthalate (PET) | 97.6 | +0.9 | +3.1 |
| PET containing 0.03 percent 5-chloro-2- 4-[2-(4-biphenylyl)vinyl]-phenyl benzofuran | 97.1 | +3.5 | −3.2 |

These results show that the shade of whiteness imparted to the polyethylene terephthalate was in the pink and blue range considered most desirable in the textile art. For the significance of the values recorded above, see R. S. Hunter, Photoelectric Color Difference Meter, J. Opt. Soc. Am., 48, 985 (1958).

We claim:

1. A normally solid, fiber and film-forming polyester or nylon polymeric material having incorporated therein approximately 0.005 to 0.5 percent by weight of said polymeric material of a fluorescent compound of the formula

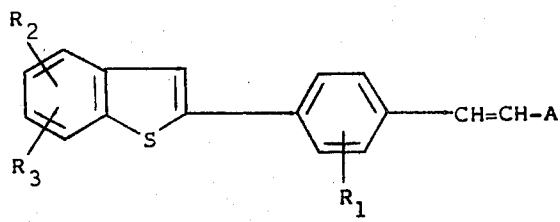

wherein $R_1$ is hydrogen, alkyl having 1 to 6 carbon atoms, alkoxy having 1 to 6 carbon atoms, or halo; $R_2$ and $R_3$ are the same or different and are members of the class consisting of H, alkyl having 1 to 6 carbon atoms, alkoxy having 1 to 6 carbon atoms, halo, dialkylamino wherein each alkyl has 1 to 6 carbon atoms, alkanoylamino having 1 to 6 carbon atoms, phenyl, phenyl substituted by alkyl having 1 to 6 carbon atoms, halo, alkoxy having 1 to 6 carbon atoms, and alkanoylamino having 1 to 6 carbon atoms; and A is a monovalent aromatic radical selected from the class consisting of 9-phenanthrenyl, 9-anthryl, 2-benzofuranyl, 2-indolyl, 2-benzothiophenyl, 3-coumarinyl, 2-indenyl, 2-quinolinyl, 3-quinolynyl, 2benzoxazolyl, 2-benzothiazolyl, 2-naphtho[2,1-b]furanyl and 2-naphtho[1,2-b]furanyl.

2. A normally solid, fiber and film-forming polyester or nylon polymeric material having incorporated therein approximately 0.005 to 0.5 percent by weight of said polymeric material of a fluorescent compound of the formula

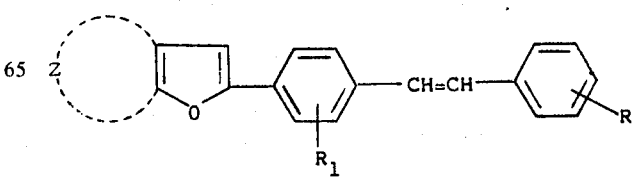

wherein R' is selected from the class consisting of H, alkyl having 1 to 6 carbon atoms, alkoxy having 1 to 6 carbon atoms, halo, dialkylamino wherein each alkyl group has 1 to 6 carbon atoms, alkanoylamino having 1 to 6 carbon atoms, phenyl, phenyl substituted by alkyl having 1 to 6 carbon atoms, halo, alkoxy having 1 to 6 carbon atoms, and alkanoylamino having 1 to 6 carbon atoms; $R_1$ is a member of the class consisting of hydrogen, alkyl having 1 to 6 carbon atoms, alkoxy having 1 to 6 carbon atoms, and halo; and Z is dibenzofurano.

3. A normally solid, fiber and film-forming polyester or nylon polymeric material having incorporated therein approximately 0.005 to 0.5 percent by weight of said polymeric material of a fluorescent compound of the formula

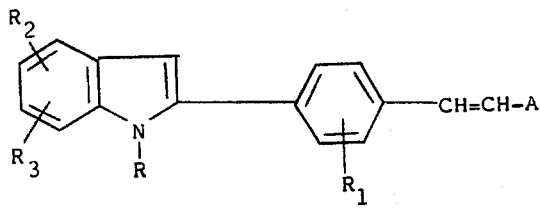

wherein R is H, alkyl having 1 to 6 carbon atoms or alkenyl having 2 to 6 carbon atoms; $R_1$ is hydrogen, alkyl having 1 to 6 carbon atoms, alkoxy having 1 to 6 carbon atoms, or halo; $R_2$ and $R_3$ are the same or different and are members of the class consisting of H, alkyl having 1 to 6 carbon atoms, alkoxy having 1 to 6 carbon atoms, halo, dialkylamino wherein each alkyl has 1 to 6 carbon atoms, alkanoylamino having 1 to 6 carbon atoms, phenyl substituted by alkyl having 1 to 6 carbon atoms, halo, alkoxy having 1 to 6 carbon atoms, and alkanoylamino having 1 to 6 carbon atoms; and A is a monovalent aromatic radical selected from the class consisting of phenyl, 2-naphthyl, 1-naphthyl, p-methoxyphenyl p-chlorophenyl, 4-biphenylyl, 9-phenanthrenyl, 9-anthryl, 2-benzofuranyl, 2-indolyl, 2-benzothiophenyl, 6-methoxy-2-naphthyl, 2-butoxy-1-naphthyl, 5-bromo-1-naphthyl, 3-coumarinyl, 2-indenyl, 2-quinolinyl, 2 pyridyl, 3-pyridyl, 4-pyridyl, 2-furanyl, 2-benzoxazolyl, 2-benzothiazolyl, 2-naphtho[2,1-b]furanyl and 2-naphtho[1,2-b]furanyl.

4. A normally solid, fiber and film-forming polyester or nylon polymeric material having incorporated therein approximately 0.005 to 0.5 percent by weight of said polymeric material of a fluorescent compound of the formula

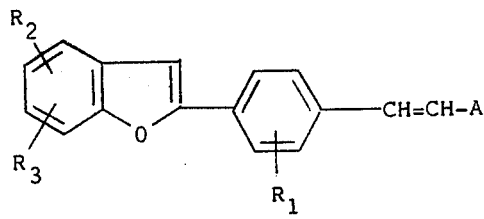

wherein $R_1$ is hydrogen, alkyl having 1 to 6 carbon atoms, alkoxy having 1 to 6 carbon atoms, or halo; $R_2$ and $R_3$ are the same or different and are members of the class consisting of H, alkyl having 1 to 6 carbon atoms, alkoxy having 1 to 6 carbon atoms, halo, dialkylamino wherein each alkyl has 1 to 6 carbon atoms, alkanoylamino having 1 to 6 carbon atoms, phenyl, phenyl substituted by alkyl having 1 to 6 carbon atoms, halo, alkoxy having 1 to 6 carbon atoms, and alkanoylamino having 1 to 6 carbon atoms; and A is a monovalent aromatic radical selected from the class consisting of 9-phenanthrenyl, 9-anthryl, 2-benzofuranyl, 2-indolyl, 2benzothiophenyl, 3-coumarinyl, 2-indenyl, 2-quinolinyl, 3-quinolinyl, 2benzoxazolyl, 2-benzothiazolyl, 2-naphtho[2,1-b]fluranyl and 2-naphtho[1,2-b] furanyl.

* * * * *

UNITED STATES PATENT AND TRADEMARK OFFICE
CERTIFICATE OF CORRECTION

PATENT NO. : 3,932,301
DATED : January 13, 1976
INVENTOR(S) : Nathan N. Crounse and Kantilal B. Desai It is certified that error appears in the above-identified patent and that said Letters Patent are hereby corrected as shown below:

Column 3, line 42, "$R^1$ are in" should read -- $R^1$ in --.

Column 5, line 19, "0°-" should read -- the --.

Column 16, Claim 1, line 55, "2benzoxazolyl" should read -- 2-benzoxazolyl --.

Column 17, Claim 3, line 33, "atoms, phenyl substituted" should read -- atoms, phenyl, phenyl substituted --.

Column 18, Claim 3, line 1, "p-methoxyphenyl" should read -- p-methoxyphenyl, --.

Column 18, Claim 4, line 35, "2benzothiophenyl" should read -- 2-benzothiophenyl --.

Column 18, Claim 4, line 36, "2benzoxazolyl" should read -- 2-benzoxazolyl --.

Column 18, Claim 4, line 37, "fluranyl" should read -- furanyl --.

Signed and Sealed this

Thirteenth Day of June 1978

[SEAL]

Attest:

RUTH C. MASON
*Attesting Officer*

DONALD W. BANNER
*Commissioner of Patents and Trademarks*